United States Patent

Baker, Jr. et al.

[11] Patent Number: 5,304,206
[45] Date of Patent: Apr. 19, 1994

[54] ACTIVATION TECHNIQUES FOR IMPLANTABLE MEDICAL DEVICE

[75] Inventors: Ross G. Baker, Jr.; Reese S. Terry, Jr., both of Houston; Alan Adkins, Angleton, all of Tex.

[73] Assignee: Cyberonics, Inc., Webster, Tex.

[21] Appl. No.: 793,842

[22] Filed: Nov. 18, 1991

[51] Int. Cl.$^5$ .............................................. A61N 1/08
[52] U.S. Cl. ........................................ 607/2; 607/45; 607/62
[58] Field of Search ............ 128/419 R, 419 C, 420.5, 128/903, 423

[56] References Cited

U.S. PATENT DOCUMENTS

| | | | |
|---|---|---|---|
| 3,236,240 | 2/1966 | Bradley | 128/903 |
| 3,344,792 | 10/1967 | Offner et al. | 128/419 R |
| 4,024,875 | 5/1977 | Putzke | 128/423 R |
| 4,102,344 | 7/1978 | Conway et al. | 128/423 R |
| 4,886,064 | 12/1989 | Strandberg | 128/903 |

Primary Examiner—William E. Kamm
Assistant Examiner—Scott M. Getzow
Attorney, Agent, or Firm—O'Connor, Cavanagh

[57] ABSTRACT

Improvements are disclosed in apparatus and techniques for activating an implantable medical device, such as a neurostimulator adapted to treat and control a disorder of a patient where the disorder is susceptible to relief in response to predetermined modulation of the electrical activity of a selected nerve or group of nerves of the patient. The neurostimulator includes a stimulus generator responsive, when activated, to generate a programmable electrical waveform, and an electrode array electrically connected to the stimulus generator for delivering the waveform to a selected nerve of the patient, such as the vagus nerve. The neurostimulator is also adapted to be programmed to provide the waveform with parameter values selected to stimulate the selected nerve to produce the predetermined modulation of the nerve's electrical activity. The neurostimulator is implemented to respond to a patient initiated signal which may be derived either manually or automatically to selectively activate the stimulus generator. Response to a manually derived signal produces a signal to trigger activation of the stimulus generator. Response to an automatically derived signal indicative of a manifestation of the disorder being treated will separately trigger activation of the stimulus generator.

13 Claims, 4 Drawing Sheets

ACTIVATION TECHNIQUES FOR IMPLANTABLE MEDICAL DEVICE

BACKGROUND OF THE INVENTION

The present invention relates generally to techniques and apparatus for activating implanted battery-operated medical devices, such as neurostimulators for treating or controlling medical, psychiatric or neurological disorders by application of modulating electrical signals to a selected nerve or nerves of the patient.

Extra-physiologic electrical stimulation of the vagus nerve for treatment of epilepsy and various forms of involuntary movement disorders is disclosed in U.S. Pat. No. 4,702,254 to J. Zabara (referred to herein as "the '254 patent"). An implantable neurocybernetic prosthesis (NCP) utilizes neurocybernetic spectral discrimination by tuning the external current of the NCP generator to the electrochemical properties of a specific group of inhibitory nerves that affect the reticular system of the brain. These nerves are embedded within a bundle of other nerves, and are selectively activated directly or indirectly by the tuning of the NCP to augment states of brain neural discharge to control convulsions or seizures. According to the patent, the spectral discrimination analysis dictates that certain electrical parameters of the NCP pulse generator be selected based on the electrochemical properties of the nerves desired to be activated.

Figure 1:
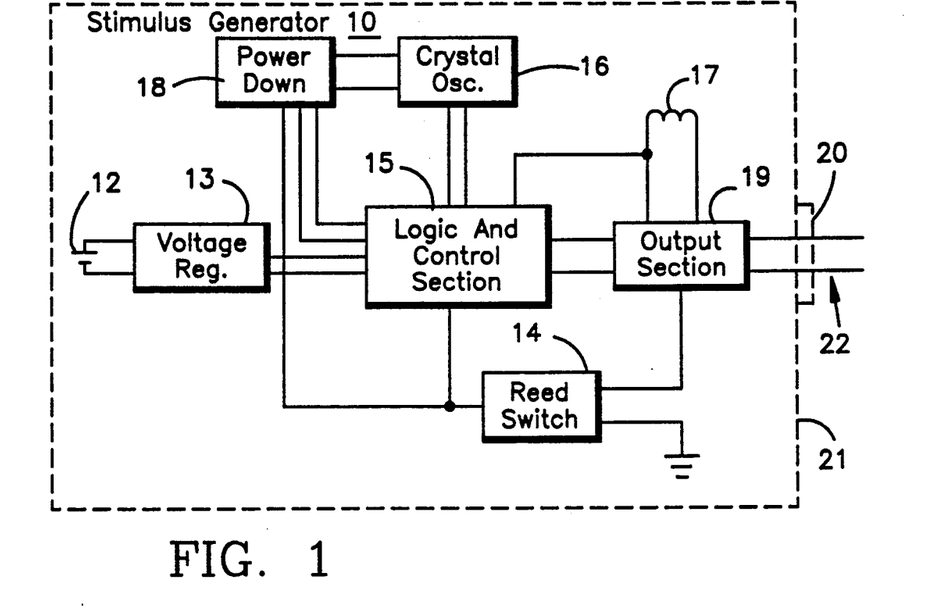
FIG. 1 is a simplified block diagram of an implantable neurostimulator (stimulus generator portion), described above.
Figure 2:
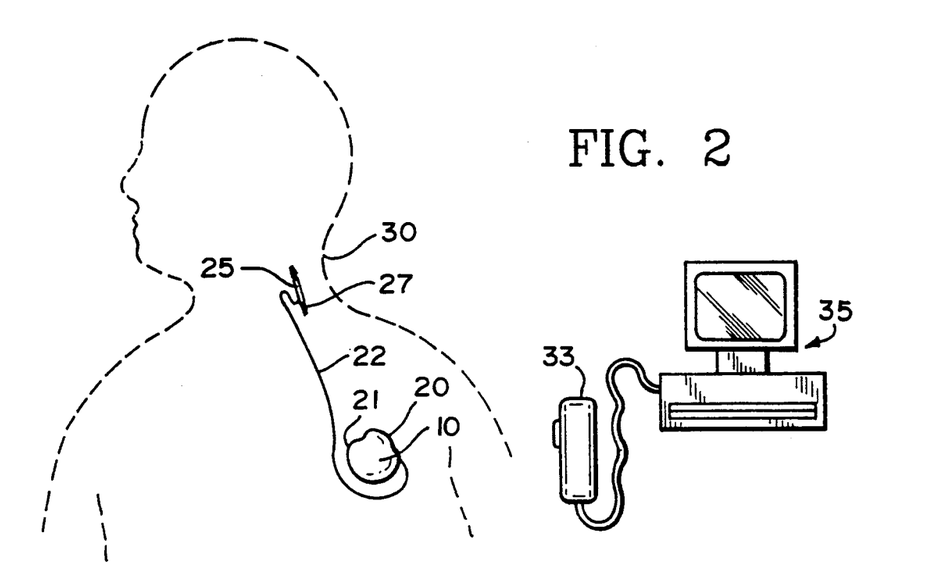
FIG. 2 is a simplified fragmentary illustration of the neurostimulator of FIG. 1 and related components implanted in the patient's body, also as described above.

An improved implantable neurostimulator device is disclosed in copending U.S. patent application Ser. No. 07/434,985, filed Nov. 10, 1989, now U.S. Pat. No. 5,154,172, issued Oct. 13, 1992 to Reese S. Terry, Jr., et al. (referred to herein as "the '172 patent), assigned to the same assignee as the instant application. The disclosure of the '172 patent is incorporated by reference herein. For the sake of convenience, a block diagram of the stimulus generator of a neurostimulator of the type disclosed in the '172 patent is illustrated in FIG. 1, and further details of location of an implantable version of the device and the associated lead/electrode system are shown in FIG. 2. The implanted device communicates with a programmer and/or monitor external to the patient's body by means of asynchronous serial communication, to control and indicate device states.

Stimulus generator 10 is implanted in the body of a patient 30 in a surgically-formed pocket immediately beneath the skin in the chest (FIG. 2). Housing 21 is hermetically sealed and composed of a material biologically compatible with the fluids and tissue of the patient's body. The neurostimulator also includes implantable stimulating electrodes 25 together with a lead system 22 for applying the output signal of the stimulus generator to a selected nerve such as the patient's vagus nerve 27. Components external to the patient's body include a programming wand 33 for telemetry of parameter changes to the stimulus generator and monitoring signals from the generator, and a computer 35 and associated software for adjustment of parameters and control of communication between the generator, the programming wand and the computer.

The stimulus generator includes a battery 12, such as a lithium thionyl chloride cell, having terminals connected to the input of a voltage regulator 13. The regulator smoothes the battery output and supplies power to logic and control section 15, which includes a microprocessor and controls the programmable functions of the device, such as current or voltage, frequency, pulse width, on-time and off-time of the output pulses generated by the genrator. The programmability allows the output pulse signal to be selectively tailored for modulating the electrical activity of the vagus nerve to produce the treatment regimen applicable to the disorder. Timing signals for the logic and control functions of the generator are provided by a crystal oscillator 16. A magnetically-actuated reed switch 14 provides the capability for patient activation of the device.

Built-in antenna 17 enables communication between the implanted stimulus generator and the external electronics (including both programming and monitoring devices) to permit the device to receive programming signals for parameter changes, and to transmit telemetry information, from and to the programming wand. Once the system is programmed, it operates continuously at the programmed settings until they are reprogrammed (by the attending physician) by means of the external computer and the programming wand.

It is important to conserve energy in any battery operated device implanted for medical treatment of a disorder. To that end, a power down circuit 18 may be electrically connected to reed switch 14 and logic/control circuit 15 and timed by the clock pulses from the crystal oscillator 16 to reduce power to the microprocessor of section 15 and/or to the oscillator to a point at which the device is essentially in a sleep state but sufficiently alert to be awakened on command. The power down mode or sleep state may be initiated automatically within a timed interval after the device has been activated to generate its programmed stimulating output signal. Alternatively, the device may stay in a reduced power state until the microprocessor is awakened by manual activation of the device by the patient.

Logic/control section 15 of the stimulus generator 10 controls an output circuit 19 which generates programmed signal levels. The programmed output signal of section 19 is fed, via an electrical connector 20 on the generator case (housing) 21, to the lead assembly 22 which is connected at its distal end to the stimulating electrodes (FIG. 2). The parameters of the stimulating signal of the implanted device are calibrated by telemetry (via the programming wand 33) according to the patient's needs, and programmed into the microprocessor for delivery of treatment upon activation of the stimulus generator.

FIG. 2 illustrates the location of generator 10 in the patient's chest with nerve electrode array 25 and associated lead 22 implanted in the patient's neck. The lead is attached at its proximal end to connector 20 of housing 21. Electrode array 25 is a bipolar stimulating electrode, for example of the type described in U.S. Pat. No. 4,573,481 to Bullara.

The implanted NCP of the '254 patent or neurostimulator disclosed in the '172 patent is activated manually or automatically to provide treatment for the duration of the seizure. The patient can manually activate the device by positioning a magnet over the implant site to actuate the reed switch at onset of the seizure. Automatic activation is triggered upon detection of instantaneous changes in certain state (EEG) parameters immediately before or at onset of a seizure. Also, a prophylactic or preventive mode may be employed in which the implanted device is activated periodically to reduce the occurrence and/or the intensity of the seizures.

It is a principal object of the present invention to provide improvements in techniques for manual and automatic activation of an implanted neurostimulator.

SUMMARY OF THE INVENTION

Rather than merely providing a magnet to be carried by the patient for manual activation of the implanted neurostimulator by applying the magnet to the external area immediately adjacent the implanted device, or adapting the device for automatic activation by periodic wakeups which are generated internally, the present invention recognizes that the availability of other or additional techniques for external control of device activation is desirable. A drawback of the current technique for manual activation, for example, is that the patient may have difficulty accessing the magnet quickly when onset of the disorder to be treated, such as an epileptic seizure, is sensed. On the other hand, specialized sensors such as EEG electrodes require complex and extremely delicate implantation procedures.

According to the present invention, apparatus for treating disorders by stimulation of a selected nerve or nerves of a patient includes, in addition to the implanted stimulus generator and electrode array and associated lead, an activation means which is responsive to a patient initiated signal to activate, or in some instances to deactivate, the stimulus generator. According to one aspect of the invention, the neurostimulator is adapted to be activated to the "on" state in response to tapping by the patient on the skin overlying the implant site. In essence, the tapping produces vibrations or pressure on the generator housing, which is readily detectable. Various types of sensors may be incorporated in the device for this purpose.

In one embodiment, the sensor is an accelerometer or a piezoelectric element (ceramic or plastic) bonded or otherwise securely mounted to the inner surface of the housing of the device, preferably directly opposite the external surface of the housing which will underlie the skin after implantation. Such an element detects vibrations of or pressure changes on the housing, so that the light taps by the patient are sensed and the sense signal is used to activate the device.

Another embodiment includes programming the device to recognize a particular coded pattern or sequence of the taps so that, for example, if the device is currently in its stimulating state the coded sequence may be used to deactivate (turn off) the device or to increase or decrease the output pulse amplitude and/or frequency. Alternatively or additionally, this capability is useful if the patient is about to perform some activity with which stimulation might interfere, by recognizing the patient's tapping sequence to delay stimulation by a preprogrammed time interval. Thus, the patient may be provided with a limited amount of control over the operation of the device, to an extent determined to be appropriate for the particular patient by the attending physician.

Automatic activation of the device by a patient-initiated signal is achieved according to the present invention by detecting an action by the patient which is indicative either of the onset or of the manifestation of the particular disorder to be treated. Thus, for example, although an imminent epileptic seizure may be detected by electrical measurements using implanted sensing (e.g., EEG) electrodes, implanted brain impedance measuring electrodes, or measurements of electrical activity of a peripheral nerve or the spinal cord, a much simpler technique for automatic activation which does not require additional implant surgery is to detect the violent movements by the patient which are characteristic of some types of seizures. The vibration sensor or accelerometer may also be used for that purpose. However, the sensitivity of the sensor must be made variable, as by programming, to permit it to be fine-tuned to the seizure characteristics of the specific patient. The desire is to assure that a seizure will be detected and the device activated to administer prompt treatment, but that the apparatus not be so sensitive that normal movements by the patient are sufficient to trigger nerve stimulation by the device.

Greater reliability of detecting violent motor activity which is characteristic of certain seizures may be achieved by locating the sensor on a limb of the patient, preferably in a bracelet to be worn on the patient's wrist. Alternative manual activation is also enhanced by incorporating a pushbutton which is readily depressed for electrical actuation of the implanted device when the patient senses a precursor or onset of the seizure. In this case, manual or automatic activation is triggered by use of miniaturized generator in the bracelet to transmit an audio or supersonic signal for detection by circuitry within the implanted neurostimulator. In one embodiment, the signal is detected by a piezoelectric device within the housing after being subjected to amplification and bandpass filtering.

Here also, the sensor, which is preferably located within the bracelet, may be an accelerometer, vibration sensor, or contact-type sensor such as mercury ball sensor in which the ball makes electrical connection with electrical contacts positioned about an internal enclosure when the patient's wrist undergoes movement. In the latter instance, the number of makes and breaks is indicative of the rapidity and violence of the movement.

Accordingly, a more specific object of the present invention is to provide means for manual and automatic activation of an implanted neurostimulator in response to patient-initiated signals indicative of a need for treatment of a disorder by nerve stimulation.

Another object is to provide apparatus for activating a neurostimulator implanted in the body of a patient to respond to and treat epileptic seizures, in which the device is adapted to detect simple indicators of the disorder.

BRIEF DESCRIPTION OF THE DRAWINGS

The above and still further objects, aspects, features and attendant advantages of the present invention will be better understood from a consideration of the ensuing detailed description of a presently preferred embodiment and method thereof, taken in conjunction with the accompanying drawings, in which.

DESCRIPTION OF THE PRESENTLY PREFERRED EMBODIMENTS

Figure 3:
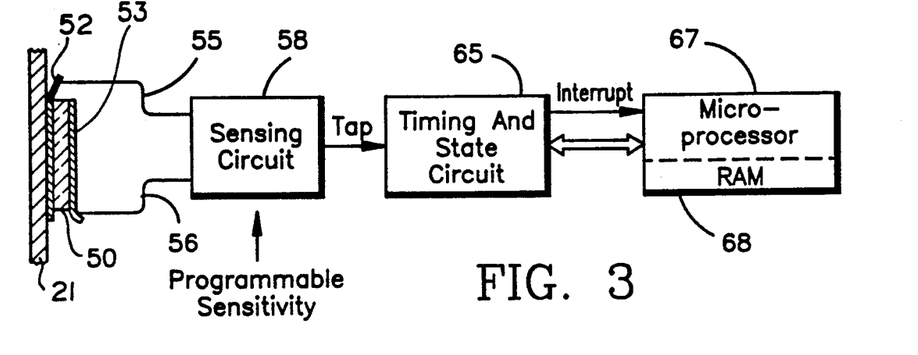
FIG. 3 is a simplified block diagram of an embodiment of the circuitry incorporated in the stimulus generator housing for manual activation of the generator according to the present invention.

Referring to FIG. 3, an embodiment of the neurostimulator device for manual activation by the patient includes a piezoelectric sensor 50 in the form of a layer of polyvinylidenefluoride (PVDF, sold under the trademark "Kynar") or ceramic, sandwiched between and secured to a pair of electrically conductive layers 52, 53. The piezoelectric sensor is bonded to the internal surface of housing 21 of the stimulus generator, opposite the external surface which will lie just beneath the skin of the patient after the device is implanted. It is desirable that the implantation procedure should produce good contact between that external surface of the housing and the tissue of the patient's body. All of the components of this embodiment which will permit manual activation are located within the stimulus generator housing.

Figures 4, 5:
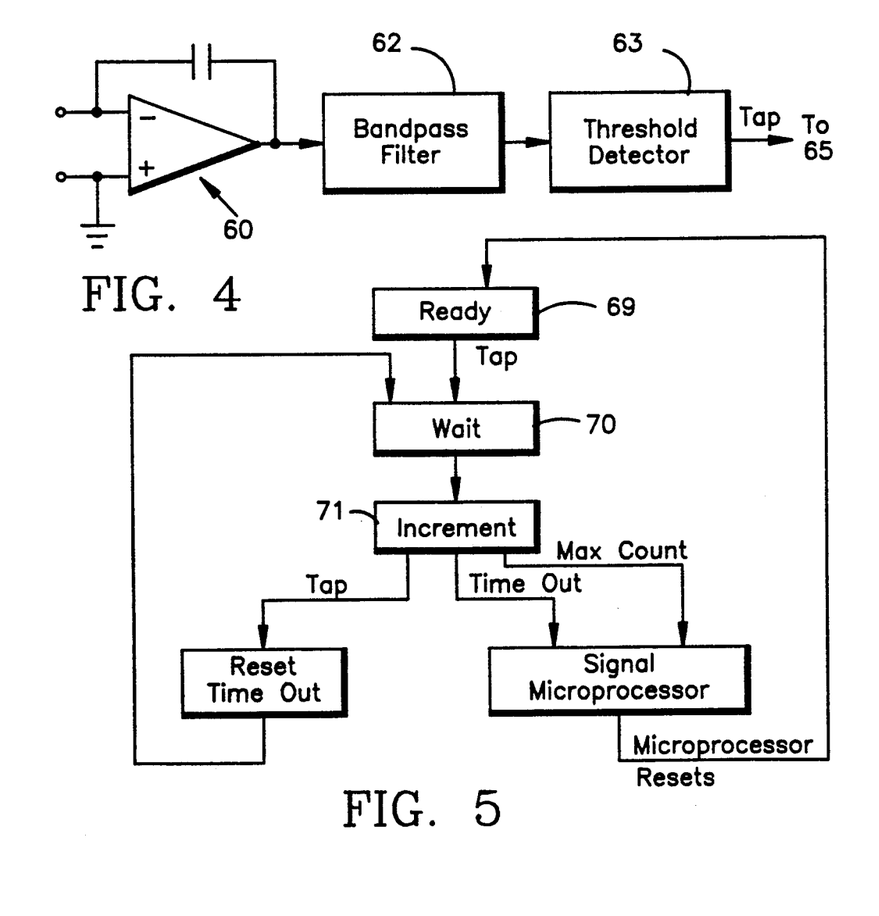
FIG. 4 is a block diagram of further details of the sensing circuit in the embodiment of FIG. 3.
FIG. 5 is a flow chart useful for explaining the operation of a portion of the embodiment of FIG. 3.

A pair of electrically conductive leads 55, 56 connected to conductive layers 52, 53, respectively, are also connected to the input terminals of a sensing circuit 58 having externally programmable sensitivity. Further details of the sensing circuit are illustrated in FIG. 4. The electrical output of the piezoelectric sensor generated as a result of mechanical forces on the layer 50 produced by taps of the patient's finger on the skin overlying the implanted housing, are applied to sensing circuit 58 via leads 55, 56. This signal is applied to a charge amplifier 60 in the sensing circuit (FIG. 4), and the amplifier output is applied to a bandpass filter 62. The filter passes signal frequencies in the range from approximately 50 to 200 Hertz (Hz). The output signal from filter 62 is delivered to a detection circuit 63 adapted to produce an output in response to an input signal exceeding the preselected threshold level of detector 63. The sensitivity of sensing circuit 58 may be varied by appropriately programming the gain of amplifier 60 and/or the threshold level of detector 63, using the external programmer.

The sensing circuit 58 helps to assure that the device will not respond to extraneous vibrations imparted to the housing and to the piezoelectric sensor from sources (e.g., normal physical activities of the patient) other than taps by the patient intended to produce manual activation of the stimulus generator. This selectivity is enhanced by a timing and state circuit 65 (FIG. 3) to which the output signal (TAP) of sensing circuit 58 is applied. Circuit 65 also receives commands from the microprocessor 67 with associated random access memory (RAM) 68 within the logic and control section of the stimulus generator.

The operation of circuit 65 will be described by reference to the flow chart of FIG. 5. Implementation of a circuit and/or software to perform the functions of the timing and state circuit according to the flow chart of FIG. 5 can be achieved in a number of well known ways. The circuit is essentially a five state machine which waits in the ready state 69 for a tap sequence to begin. During the ready state a counter used to accumulate the number of taps in a sequence is held in the cleared state. Another counter which simply accumulates time since the last tap in a sequence is also held cleared.

Detection of a tap moves the state machine to the waiting state 70. The time counter begins running. This state serves to "debounce" the detection of a tap, which improves the chance that each tap is detected as a single event. On expiration of 100 milliseconds on the time counter, for example, the state machine enters the increment state 71. In this state, the tap counter is incremented to register the detection of each individual tap. The state is exited upon occurrence of any of three different conditions.

If a tap occurs before either of the other two exit conditions, the counter which is counting time between taps is cleared (reset time out 72) and the machine then re-enters the waiting state 70. The other two conditions for exit from the increment state are detection of the maximum allowed count of taps, and elapse of the time-out period which is set, for example, to a value of about 1.5 seconds. If no further taps are detected during this time interval, the tap sequence is assumed to be over. Occurrence of either of the latter two exit conditions will cause an interrupt or flagging of the microprocessor (state 73) in the logic and control section.

The microprocessor reads the number of taps in the sequence (i.e., the tap count since the last reset), and acts upon the command represented by a sequence of taps of that number. When it is ready to receive new commands, the microprocessor resets the state machine to the ready state 69.

The most elementary commands are represented simply by numbers of taps counted. A one count may, for example, be treated as a probable accident, and ignored. On the other hand, a sequence of two or three taps may be used to trigger the output of a programmed burst from the output section by the microprocessor in the logic and control section. A sequence of four or five taps is used, for example, to turn off any burst in progress. Finally, a sequence of seven taps may be used to deactivate the device indefinitely, such as for an entire twenty-four hour period.

A more complex set of commands can be developed by additional use of the external magnet to activate the reed switch in the device. For example, a sequence of taps occurring while the reed switch is continuously closed may be used to encode the type of reprogramming requested. Any odd count may be ignored, while a count of two can be used to denote that the amplitude is to be decreased by a predetermined value, a count of four that the frequency is to be decreased by a set percentage, a count of six that amplitude is to be increased by a predetermined value, and a count of eight that the frequency is to be increased by a set percentage. These changes may be commenced immediately, or, if desired, may be delayed pending further refinement by elaborating input consisting of a tap sequence without closure of the reed switch within a specified time interval.

In this way, the implanted device is readily activated, controlled and may even be reprogrammed in appropriate cases by the patient by application of sequences of light taps on the skin overlying the implanted device. There is no need to carry a magnet or other obtrusive device for use in activating the neurostimulator, or to locate the magnet when it is needed for that purpose, unless the magnet is to be used in combination with the taps for the more complicated commands. Also, the implanted device is readily programmed to recognize different coded patterns or sequences of taps by the patient, to do such things as turning off the device if it is currently in the stimulating mode, or to increase or decrease the intensity and/or frequency of the stimulation, or even to delay the initiation of stimulation for a selected time interval.

Figures 6, 7:
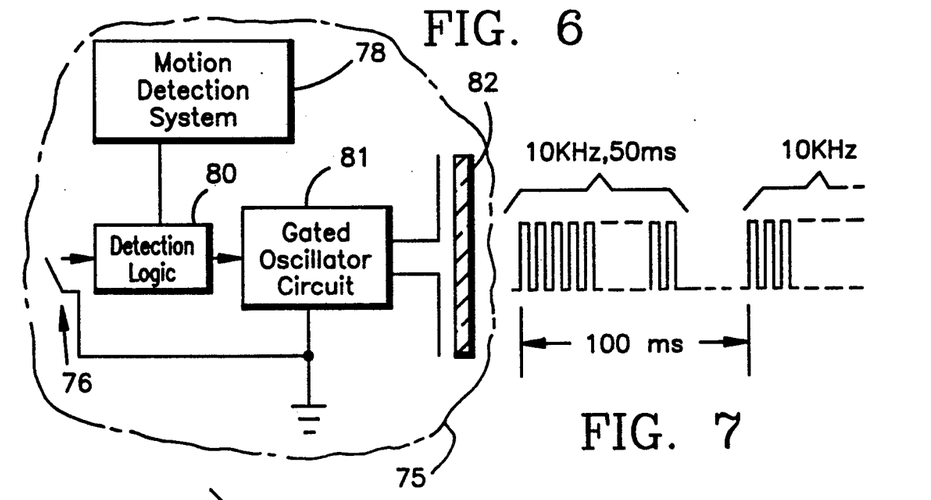
FIG. 6 is a simplified block diagram of another embodiment of a detection system for activating an implanted neurostimulator, both manually and automatically.
FIG. 7 is a pulse waveform generated by a portion of the circuit of FIG. 6.

Another embodiment of the invention for convenient manual activation of the implanted neurostimulator by the patient, and which is also useful for automatic activation in the case of an epileptic or other patient whose seizures produce violent movements and are treatable by nerve stimulation, is depicted in FIG. 6. Part of the activation electronics are incorporated within a bracelet to be worn on the wrist of the patient. A wrist bracelet is a desirable location for two reasons. It is easily accessible by the patient for manual activation of the neurostimulator, and, in cases where the patient suffers from violent motor seizures, the positioning of a motion sensing device on a limb of the patient is more reliable for purposes of automatic activation.

In the embodiment of FIG. 6, the bracelet 75 (shown in fragmentary phantom lines) has incorporated therein a pushbutton switch 76, motion detection system 78, detection logic 80, and gated oscillator circuit 81. The electronics are readily fabricated in miniaturized form in a semiconductor integrated circuit. The power source for the device may be a battery such as a conventional watch-type battery, and preferably a lithium cell, which is of a size and capacity readily accommodated within the bracelet. Whether manually triggered by depressing the pushbutton switch or automatically triggered by a signal generated by the motion detector, the detection logic circuit 80 determines that the nature of its input signal is indicative of a need to activate the implanted neurostimulator. The logic circuit then provides an enabling input to gated oscillator 81 which produces a series of pulse trains each having a duration of about 50 milliseconds (ms) and a repetition rate (frequency) of about 10 kilohertz (Khz), with an off-time of 50 ms so that the cycle of consecutive trains is 100 ms, for example, as shown in FIG. 7.

Figure 8:
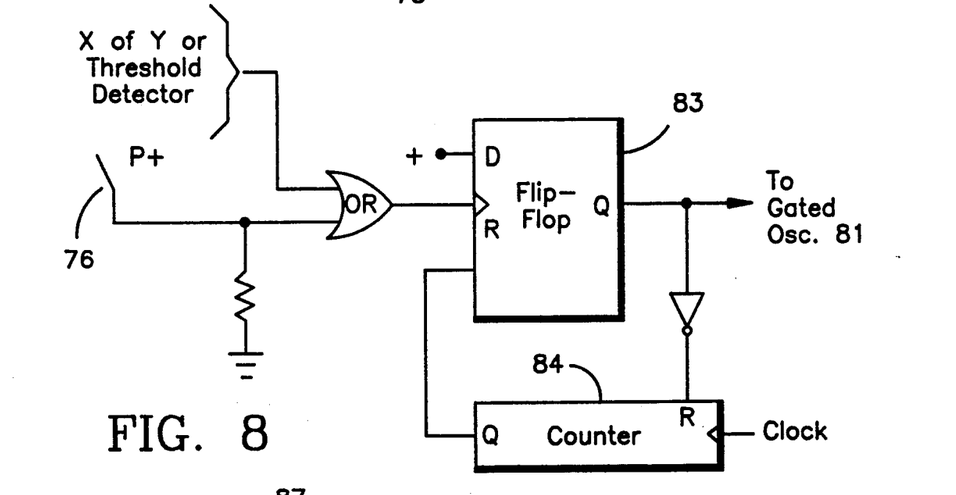
FIG. 8 is an embodiment of a detection logic circuit for use in the circuit of FIG. 6.
Figure 10:
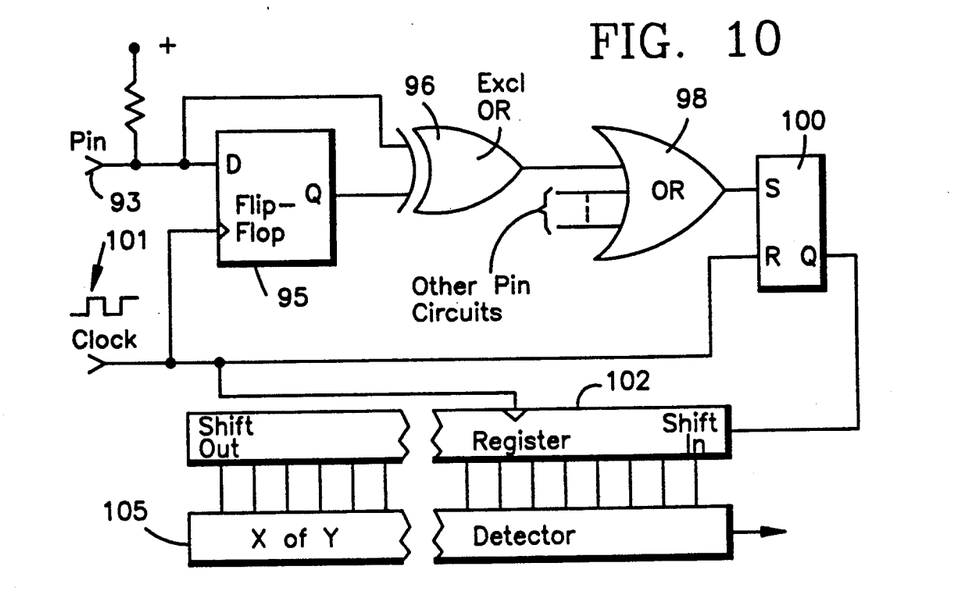
FIG. 10 is a simplified block diagram of one embodiment of a detection system f or use as part of the motion detection system in the circuit of FIG. 6.

Referring to the detailed detection logic illustrated in FIG. 8, such operation is triggered by either detected motion from a system 78 in the form of a logic true level from the X out of Y detector of FIG. 10 or a threshold detection from the circuit of FIG. 11 (both of which will be described in detail presently), or by manual closure of the activation pushbutton 76 on the bracelet, which causes a flip-flop 83 to be reset. This in turn activates gated oscillator 81 and starts the count of another time counter 84. When the latter counter overflows, such as at a count indicative of an elapsed time interval of 250 ms, the latch 83 is reset and the gated oscillator is shut off.

The gated oscillator output waveform is preferably of either audio frequency or ultrasonic frequency, for purposes of activating the neurostimulator. This output is applied to a ceramic piezoelectric transducer 82 such as that of the general type illustrated in FIG. 6, on the case of the wrist bracelet 75. The transducer is on the inside surface of the bracelet, in good contact with the patient's skin at the wrist. The purpose is to couple the sound signal produced directly into the arm through the transducer, so that transmission proceeds directly through the bulk of the limb into the trunk, where it is received by a transducer (not shown) affixed to the inside surface of the case of the implanted stimulus generator. The signal may be boosted to detectable levels by use of a tuned amplifier within the stimulus generator case. A characteristic 50 ms on/50 ms off pattern is detected to maximize noise immunity, with three "on" phases separated by two "off" phases providing a reasonable key.

The tuned amplifier acts as a high Q filter centered near or at the highest frequency (e.g., 10 KHz). The receiving system is adapted to look for alternating on and off periods at the correct repetition rate (here, 10 Hz; i.e., bursts of 10 KHz repeat at a 10 Hz rate). These safeguards are intended to assure that the neurostimulator is activated or otherwise controlled (such as to increase the intensity or frequency of the stimulation, deactivate the device or delay the stimulation) only by the appropriate signal, and not by false signals.

A motion sensor is provided within the bracelet for automatically detecting movements by the patient. The motion sensor portion of the detection system 78 (FIG. 6) may be of any known type, such as an accelerometer or a vibration sensor, but preferably, is a contact-type sensor as shown in principal part in FIG. 9. A conductive ball such as a mercury ball makes electrical connection between adjacent electrical contacts positioned about an otherwise electrically insulative enclosure when the patient's wrist undergoes movement. In the contact-type sensor, the number of makes and breaks and specific location of the contacts is indicative of the rapidity and violence of the patient's movements at the wrist location.

Figures 9A, 9B:
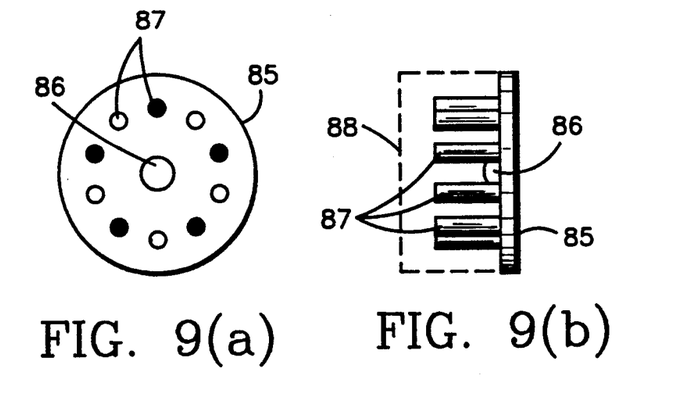
FIGS. 9a, 9b are exemplary embodiments of a motion sensor for use in the circuit of FIG. 6.

As shown in FIG. 9(a) and (b), which are top and side views, respectively, of the interior of such a contact-type sensor, an electrically insulative wall (floor) 85 of the enclosure 88 on which the rolling mercury ball 86 moves is covered with spaced-apart electrical contact posts or pins (electrodes) 87. The spacing between the pins is just less than the width of the ball 86 resting on the floor surface, so that adjacent electrodes will be shorted by the ball when it encounters them. Alternate ones of the pins are grounded, as indicated by the dark circles in FIG. 9(a), and the others are used for sensing.

Motion of the patient's wrist causes the ball 86 to move about surface 85, and in the process to bridge adjacent pairs of the pins 87. Each sensing pin is passively pulled up to the positive supply. The sensor output is applied to an X of Y detection system such as that shown in FIG. 10,, as the processing portion of the motion detection system.

The circuit of FIG. 10 operates as follows. A flip-flop 95 associated with each pin, such as 93, stores the state of the input at the time of last sampling. An exclusive-OR function 96 compares the stored value with the current value, and, if the two differ, produces a logic true output. The outputs of all of the pin monitoring circuits are OR'ed together by OR gate 98 at the set input of a set/reset flip-flop 100. If the logic state of any pin changes while this flip-flop is not being reset, the presence of a state change is recorded. Once in each clock period 101 (for example, nominally each 40 ms) this information is shifted into a register 102 which has a bit representing the presence of an input state transition for each of the latest N clock periods. The parallel outputs of the shift register are monitored by an X of Y detector 105 and, if a high enough percentage (X of Y) show state changes, this constitutes recognition that motion of the type to cause triggering of activation has been detected.

The same clock edge that clocks the logic level of the set/reset flip-flop 100 into the register 102 clocks the current state of the input pin into flip-flop 95 which stores the last value. The phase of the clock which begins with this edge resets the set/reset flip-flop to a zero level. This clock phase is preferably shorter than the complementary phase to maximize the percentage of time during which the system is sensitive to state changes.

If vigorous motion occurs, the conductive ball will roll around and make contact in rather random fashion with pairs of pins. The more vigorous the motion, the higher the percentage of time that different pins will be affected, and the higher the probability that a pin state transition will be detected during any given sampling interval. This, in turn, increases the probability that the X of Y detector will detect an event.

The X of Y detector may be implemented in hardware or software. In a hardware implementation, the length of the shift register is Y+b 1. A running count of the number of 1's in the first Y bits is maintained using an accumulator and an adder. Each time a new state enters the shift register, a comparison is made with the oldest bit. If the oldest bit in the register is the same as the newest bit, the value in the accumulator remains unchanged. If the oldest bit is different, the accumulator is either incremented (when the newest bit is a 1 and the oldest bit a 0), or decremented (when the newest bit is a 0 and the oldest bit a 1). If the accumulator reaches the threshold, then seizure detection is declared and the stimulus generator is activated to generate its treatment.

Figure 11A:
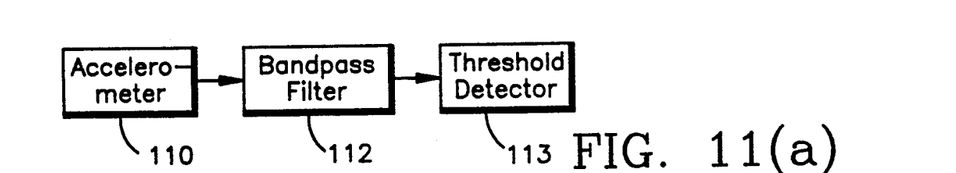
FIG. 11a, 11b are simplified block diagrams of another embodiment of a detection system for use as part of the motion detection system in the circuit of FIG. 6.

If motion is detected using an accelerometer, a threshold detection system such as that shown in FIG. 11 may be used as the processing portion of the motion detection system, to trigger activation of the stimulus generator. FIG. 11(a) is exemplary of the use of a one-dimensional accelerometer (not the mercury ball contact sensor described above) to sense motion. In this case, the acceleration signal is subjected to bandpass filtering in filter 112 followed by threshold detection by detector 113. Additional benefit can be derived in the signal processing function by an envelope detection followed by low pass filtering immediately before the threshold detection by detector 113, to reduce or eliminate responses to occasional brief but forceful accelerations arising from impact.

Figure 11B:
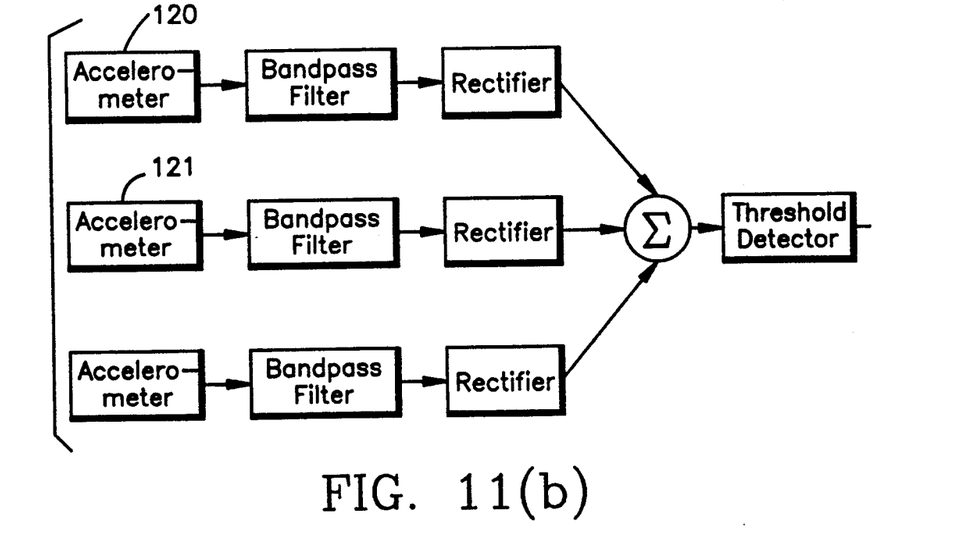

The more ideal case of three-dimensional motion sensing with threshold detection is illustrated in the circuit of FIG. 11(b). The signal from orthogonal accelerometers 120, 121, and 122 are bandpass filtered, rectified and combined, and the combination subjected to threshold detection, to provide a more realistic indication of forces on the bracelet of the type which should trigger the activation (or a more selective output) of the stimulus generator. If even greater accuracy were necessary, it could be provided by processing to calculate the square root of the sum of the squares of the three acceleration signals.

While the motion detection system is shown as being implemented at least in part external to the patient's body, which is preferred because of the greater reliability of detection of violent movements associated with certain seizures, the motion detection system may instead be incorporated within the housing of the implanted stimulus generator, or be implanted in the patient's body within its own separate case.

Although certain preferred embodiments and techniques for manual and automatic activation of an implanted neurostimulator have been described herein, it will be apparent to persons skilled in the field of the invention, from a consideration of the foregoing disclosure, that variations and modifications of these embodiments and techniques may be made without departing from the spirit and scope of the invention. For example, the principles of the invention are applicable in at least some respects to other implantable medical devices as well. Accordingly, it is intended that the invention shall be limited only to the extent required by the appended claims and the rules and principles of applicable law.

In the context of the disclosure and the claims, the terminology "signal initiated by the patient" or "patient initiated signal" is intended to mean and refer to signals which are manually produced by the patient by means which are part of or worn by the patient (in contrast to the requirement of a separate device such as a magnet), or to signals which are automatically produced as a result of an external manifestation of the disorder by the patient (in contrast to an internal parameter such as EEG changes).

What is claimed is:

1. A medical device for treating a disorder of a patient, comprising:
   implantable electronic means operative when activated for developing a predetermined therapy to treat the disorder,
   implantable delivery means connectable to the electronic means for delivering said therapy to a selected region of the patient's body, and
   activation means responsive to a signal initiated by the patient for activating the electronic means to cause the delivery of the therapy by the delivery means, when connected to the electronic means, to the selected body region and thereby to treat the disorder, the activation means including
   detection means responsive to tapping by the patient in at least one coded sequence of taps on the skin adjacent the implanted electronic means for manual activation thereof, and
   adjustment means for varying a preselected parameter of the therapy in response to another coded sequence of taps.

2. A medical device for treating a disorder of a patient, comprising:
   implantable electronic means operative when activated for developing a predetermined therapy to treat the disorder,
   implantable delivery means connectable to the electronic means for delivering said therapy to a selected region of the patient's body, and
   activation means responsive to a signal initiated by the patient for activating the electronic means to cause the delivery of the therapy by the delivery means, when connected to the electronic means, to the selected body region and thereby to treat the disorder, the activation means including detection means responsive to tapping by the patient in at least one coded sequence of taps on the skin adjacent the implanted electronic means for manual activation thereof, and deactivating means responsive to another coded sequence of taps while the electronic means is activated for deactivating the electronic means.

3. A medical device for treating a disorder of a patient, comprising:

implantable electronic means operative when activated for developing a predetermined therapy to treat the disorder, implantable delivery means connectable to the electronic means for delivering said therapy to a selected region of the patient's body, and activation means responsive to a signal initiated by the patient for activating the electronic means after a predetermined delay interval to cause the delivery of the therapy by the delivery means, when connected to the electronic means, to the selected body region and thereby to treat the disorder.

4. A neurostimulator for treating a disorder of a patient manifested by seizures characterized by violent disorganized movements of the patient, comprising:

implantable electronic means operative when activated for developing a predetermined therapy to treat the disorder, including signal generator means for generating a programmed electrical stimulus comprising the therapy, implantable delivery means connectable to the generator means adapted to deliver said stimulus to a preselected nerve of the patient, and activation means including motion sensor means responsive to said movements by the patient for automatically activating the electronic means to cause delivery of said stimulus by the delivery means to said preselected nerve when the delivery means is connected to the generator means, whereby to treat the disorder, and selection means for precluding activation of the electronic means in response to detection of movements by the patient which are characteristic of normal physical activity by the patient and not of the violent disorganized type associated with a seizure.

5. The invention of claim 4, wherein the selection means includes sensitivity means for determining the violence of the movements.

6. The invention of claim 5, wherein the motion sensor means produces an electrical signal indicative of frequency of movements by the patient, and the sensitivity means includes an electrical signal filter for limiting the electrical signal to a predetermined frequency band.

7. The invention of claim 5, wherein the motion sensor means produces an electrical signal indicative of the frequency of making and breaking of electrical contacts in response to movements by the patient, and the sensitivity means includes a counter to ascertain the number of contacts made during a predetermined interval of the movements.

8. The invention of claim 4, wherein the implantable electronic means has a housing, and the activation means is located within the housing.

9. A medical device for treating a disorder of a patient, comprising:

implantable electronic means operative when activated for developing a predetermined therapy to treat the disorder, implantable delivery means connectable to the electronic means for delivering said therapy to a selected region of the patient's body, and activation means responsive to a signal initiated by the patient for activating the electronic means to cause the delivery of the therapy by the delivery means to the selected body region when the delivery means is connected to the electronic means, whereby to treat the disorder, the activation means comprising a bracelet including manual signalling means for producing a signal in the range of one of audio and ultrasonic frequencies.

10. The invention of claim 9, wherein the bracelet further includes sensing means responsive to a physiological manifestation of the disorder being treated for producing a signal to automatically activate the electronic means.

11. The invention of claim 10, wherein the implantable electronic means has a housing, and the activation means further includes receiving means located within the housing and responsive to the signal produced by the sensing means for ascertaining whether the signal is indicative of a physiological manifestation of the disorder being treated in contrast to a similar physiological manifestation of a normal reaction, and limiting activation of the electronic means only in response to the former physiological manifestation.

12. The invention of claim 11, further including means external to the patient for selectively adjusting the sensitivity of the receiving means to the signal produced by the sensing means.

13. Neurostimulator apparatus for treating and controlling a disorder of a patient susceptible to relief in response to predetermined modulation of the electrical activity of a selected nerve or group of nerves of the patient, including a stimulus generator adapted for implantation and responsive, when activated, to generate a programmable electrical waveform, an electrode array adapted for implantation and electrical connection to the stimulus generator for delivering the waveform to a selected nerve of the patient, said stimulus generator being programmable to provide the waveform with parameter values selected to stimulate the selected nerve to modulate the electrical activity thereof according to said predetermined modulation, and activation means responsive to a patient initiated signal which may be derived both manually and automatically for selectively activating the stimulus generator, the activation means including means responsive to a manually derived signal for producing a signal to trigger activation of the stimulus generator, and means responsive to an automatically derived signal for verifying that the automatically derived signal is indicative of a manifestation of the disorder being treated before activating the stimulus generator.

* * * * *